United States Patent [19]

Stanko

[11] Patent Number: 5,172,698
[45] Date of Patent: Dec. 22, 1992

[54] TELEPHONIC PACEMAKER AND SINGLE CHANNEL EKG MONITORING DEVICE

[76] Inventor: Bruce E. Stanko, 4284 Lampl Rd., Allison Park, Pa. 15101

[21] Appl. No.: 528,839

[22] Filed: May 24, 1990

[51] Int. Cl.$^5$ ............................................. A61N 1/08
[52] U.S. Cl. .................................. 128/697; 128/903; 128/904
[58] Field of Search ............... 128/903, 904, 710, 696, 128/697

[56] References Cited

U.S. PATENT DOCUMENTS

| | | | |
|---|---|---|---|
| 3,885,552 | 5/1975 | Kennedy | 128/904 |
| 4,596,256 | 6/1986 | Ascher et al. | 128/710 |
| 4,883,064 | 11/1989 | Olson et al. | 128/904 |

FOREIGN PATENT DOCUMENTS 3636996  11/1987  Fed. Rep. of Germany ...... 128/710

Primary Examiner—Kyle L. Howell
Assistant Examiner—Scott M. Getzow
Attorney, Agent, or Firm—Reed Smith Shaw & McClay

[57] ABSTRACT

The telephonic pacemaker monitoring device of the present invention eliminates the need for external electrodes that wrap around the fingers or wrists, or make contact with the skin on the chest. The monitoring unit has four finger touchpads and a communications station including a transmitter and a visual display located on the face of the device. The monitoring device also has a feedback system which enables the operator at the receiving center to immediately notify the patient via the visual display if a proper transmission or a faulty transmission is occurring. The feedback system and the visual display also enable the operator at the receiving center to notify the patient if increased finger pressure on the touchpads is needed or if the telephone handset should be picked-up for verbal communication. This feedback system and visual display eliminate the delay in notifying the patient that a faulty transmission has occurred. The present unit can also be used as a portable single channel telephonic EKG monitor which can be used by ambulances, paramedics, and other trained personnel at public gatherings.

18 Claims, 3 Drawing Sheets

TELEPHONIC PACEMAKER AND SINGLE CHANNEL EKG MONITORING DEVICE

FIELD OF THE INVENTION

The present invention relates to a telephonic pacemaker monitoring device for remote pacemaker monitoring. It is particularly useful in obtaining follow-up information on those patients that have been implanted with a cardiac pacer apparatus more commonly called a pacemaker.

BACKGROUND OF THE INVENTION

It is important to monitor a pacemaker during its life to determine how the pacemaker is functioning including its operating parameters as well as determining the end of its battery's life. Through telephonic monitoring, typically using a small, portable monitoring device and a telephone, a patient can remain at home while the doctor or physician can still obtain this information. A signal corresponding to the pacemaker output is produced by the remote monitoring device, then sent through the telephone lines to a receiving center located at a hospital, clinic or doctor's office. This signal can then be read by a qualified person to determine the necessary information about the pacemaker such as its pulse rate, pulse width and magnetic rate. The present pulse rate of the pacemaker can be compared to the original pulse rate at implant or to a subsequently programmed pulse rate. Any deviation in the pacemaker pulse rate could indicate a potential problem with the pacemaker and appropriate corrective measures can be taken by the physician. Similarly, the pacemaker pulse width can be telephonically monitored and compared to the original pulse width of the pacemaker at implant or to a programmed pulse width. The magnetic rate of the pacemaker can be measured by placing a magnet on the patient's chest over the pacemaker implant location causing the pacemaker to operate in a magnetic rate mode. In many pacemakers the magnetic rate is used to determine battery life by calculating the percentage increase or decrease in the magnetic rate. Since magnetic rate fluctuation is gradual, telephonic monitoring, permits early detection of premature battery depletion, and steps for replacement can be made to provide maximum patient safety.

Patients with implanted pacemakers are typically monitored over the telephone using the following procedure. The patient is given a small, portable telephonic monitoring device, typically about the size of a transistor radio. This monitor is used to transmit vital pacemaker signals by telephone to a receiving center. By sending a beeping tone from the monitor over the telephone lines, pacemaker parameters such as pulse rate, pulse width and magnetic rate, can be determined by the physician or clinician at the receiving center who is able to confirm that the pacemaker is functioning properly. A receiving center typically consists of an EKG processing module, a phone boot for the receiving center telephone, and a built-in thermal printer for operator analysis of an EKG strip chart which shows the pacemaker functioning.

Current pacemaker monitoring devices are shown and described in U.S. Pat. Nos. 4,622,979 and 3,885,552, as well as in the operating instructions for a device manufactured by Instromedix ® of Hillsboro, Oreg. called the Pacer-Tracer ®. In order for the patient to operate these monitors, electrodes are needed to transmit the desired signals from the pacemaker to the monitoring devices. There are three basic types of electrodes currently being used, namely fingertip electrodes, wrist electrodes and chest electrodes. Fingertip electrodes are usually conductive pads that wrap around the tips of the index fingers. These pads are connected to wires which plug into jacks in the monitor. Wrist electrodes are similar to fingertip electrodes but are placed on both wrists and are usually made of conductive material attached to a flexible and expandable wristband. In the chest electrode monitor, the four chest electrodes can actually be part of the monitor and act as "feet" on the bottom of the unit. The monitor is placed over the patient's chest with the four electrode feet making contact with the patient's skin to transmit the signal. All three of the current methods of electrode placement, however, are inconvenient for elderly patients to use, especially when one considers that they must first speak over the telephone and second place the telephone handset over the monitor without dislodging the electrodes which may be located on either their fingers, wrists or chest.

The inconvenience of these electrodes is compounded when the magnetic rate of the pacemaker is transmitted. To have the pacemaker operate in the magnetic mode, a magnet must also be placed on the patient's chest, over the pacemaker location. This is not easily accomplished when the patient is also trying to place the telephone receiver over the monitor to transmit the pacemaker signals while not dislodging the electrodes from either their fingers, wrists or chest. Also, it is important to keep the magnet fairly still and positioned over the pacemaker to obtain an accurate reading of the magnetic mode.

Another disadvantage with the current monitoring devices is that there is no convenient way for the patient to know whether the pacemaker signals are being transmitted properly. This can be frustrating not only to the patient, but also to the operator or clinician reading the signals at the receiving center. One method currently being used is for the operator to observe a faulty or improper set of signals and to push a patient alert button at the receiving center which sends a loud buzzing sound over the telephone line. This sound emanates from the telephone handset or receiver and is supposed to notify the patient that the is to pickup the handset. Several problems exist, however, with this audio patient alert system. For example, the patient usually has the telephone handset over the monitor and cannot hear the loud buzz from the handset. Also, since most patients are elderly, hearing the buzzing sound is often a problem.

It would be desirable, therefore, to have a telephonic pacemaker monitoring device which did not have the above-described disadvantages and which could also function as a single channel EKG.

SUMMARY OF THE INVENTION

Generally, the present invention relates to a telephonic pacemaker monitoring device which overcomes the disadvantages described above by placing at least three and preferably four electrode touchpads on the face of the monitoring unit. These electrode touchpads are preferably arranged in a generally U-shaped or V-shaped configuration. They are similar to the touchpads on a calculator, but are made of a conductive material so that the electronic circuitry in the unit can detect the pacemaker signals or the patient's pulse by simply placing fingers from each of the patient's hands on one of the touchpads. Two of the touchpads are preferably connected together and used as reference electrodes. This design eliminates the need for external electrode wires as required by the fingertip and wrist electrodes. It also eliminates the need to hold the monitor over the patient's chest with one hand while placing the telephone handset against the monitor with the other hand, as is necessary with the chest electrode monitor.

Another advantage of the present invention is a feedback system which enables the operator at the receiving center to determine if the pacemaker signal is being transmitted properly to the receiving center and inform the patient of this through a visual display, preferably located on the upper surface or face of the monitoring unit. The operator can elect to send a multi-frequency tone generated by the telephone unit at the receiving center to the patient's monitor, which, depending on the tone selected, will activate one or more LEDs located in the visual display. Preferably a red or green light on the display is visible to the patient with a label associated therewith. This is especially useful since the transmission time for the pacemaker signals is usually 60 seconds, and the entire transmission could be malfunctioning and invalid because of poor electrode placement or low battery voltage. Having a visual feedback signal displayed on the face of the monitoring device eliminates the long delay in notifying the patient of a faulty transmission.

The present invention also has the capability of functioning as a single-channel EKG monitor since it detects and transmits the patient's pulse. The device can be used with any method of telecommunications currently available such as a regular telephone system, a cellular telephone or a mobile phone. As a result, it can be used by paramedics or ambulance personnel at stadiums, malls, airplanes, department stores, or any public gathering places. Densely populated public gathering areas create a large population of people with potential for cardiovascular emergencies, and little chance for immediate medical evaluation. For example, if a sports fan develops chest discomfort at a game after consuming food and drink, a rapid evaluation of his EKG may provide information that could be life saving. Used in this way, the present invention can provide medical personnel with the patient's heart rate and rhythm through a single channel EKG. The presence or absence of abnormal atrial or ventricular beats and myocardial infarction can be ascertained from the single channel EKG tracing. With this information, the need for emergency evaluation or treatment can be estimated with an expediency and accuracy not presently available.

Generally, the present invention relates to a remote pacemaker monitoring device comprising a single portable unit wherein at least three electrically conductive finger touchpads are located on the outside surface of the unit, preferably on its face. Also located on the outer surface of the unit and preferably on its face is a two-way communications station, preferably comprising a transmitter for sending out pacemaker or EKG information via a communications means, and a visual display for communication information from the central receiving center to the patient. Within the unit a detection and transmission circuit is electrically connected between the electrically conductive touchpads and the transmitter located on an outer surface of the unit for detecting pacemaker signals or a patient's pulse and transmitting them to a receiving center via the communication means. Also within the unit is a decoder circuit electrically connected between the visual display and an audio detector, such as a microphone, located on the unit for providing visual feedback via the communication means from the receiving center to the patient. Preferably the communication means is a telephone system, in which case the transmitter and the audio detector are located such that they are in close proximity to the corresponding portions of the telephone handset.

Other details, objects and advantages of the present invention will become apparent as the following description of the presently preferred embodiment of practicing the invention proceeds.

BRIEF DESCRIPTION OF THE DRAWINGS

In the accompanying drawings, preferred embodiment of the present invention are illustrated wherein.

DETAILED DESCRIPTION OF THE INVENTION

Figure 1:
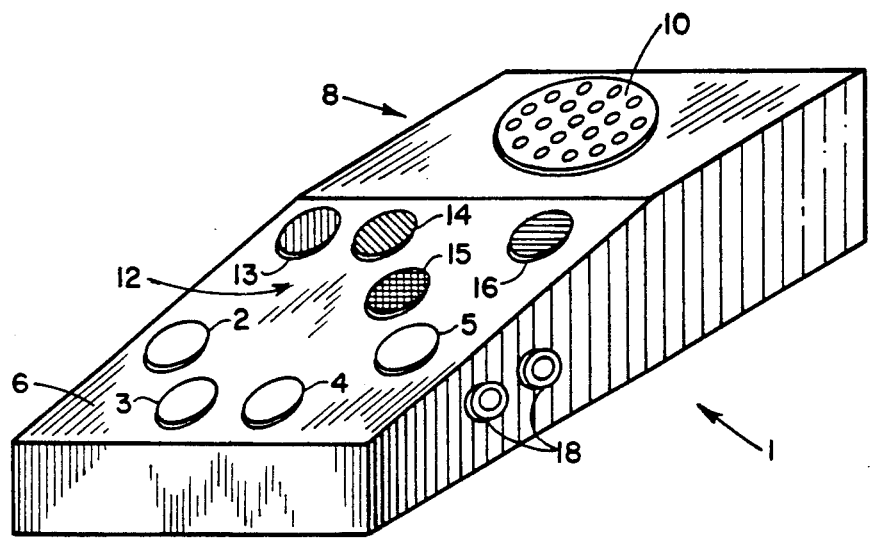
FIG. 1 shows a perspective view of the monitoring device of the present invention.
Figure 2:
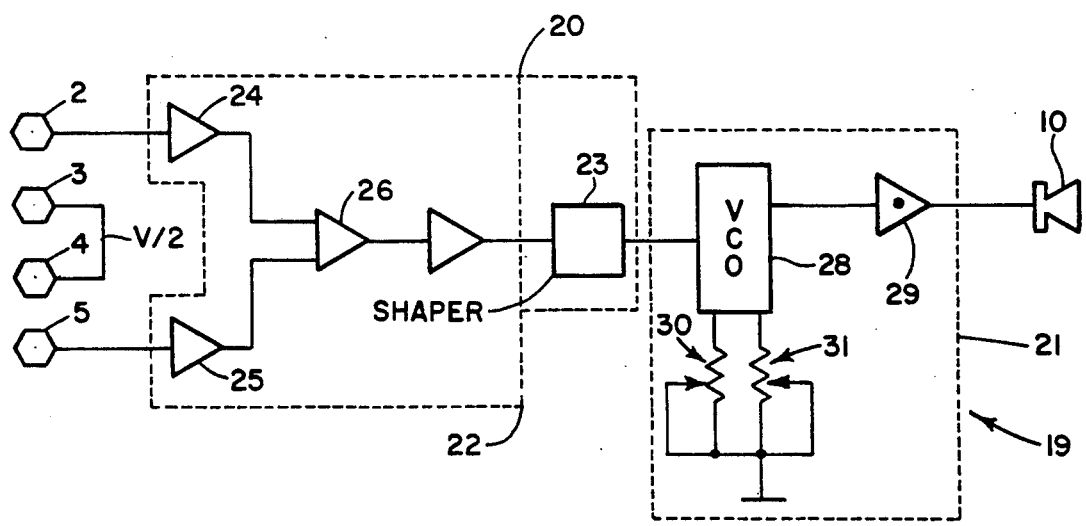
FIG. 2 is a block diagram of the detection and transmission circuit.

FIG. 1 shows a preferred embodiment of the pacemaker monitoring unit 1 of the present invention. This portable unit is preferably 3 in.×6 in.×2 in. At least three electrically conductive finger touchpads 2, 3 and 5 are placed on the face 6 of the unit 1, preferably at the front portion thereof for easy access and use by the patient. The finger touchpads are preferably arranged in a generally U-shaped or V-shaped configuration although other configurations can be used. Two of the finger touchpads are used to generate the patient or pacemaker signals to be monitored while the third acts as a reference point. Preferably, a fourth finger touchpad is used for the convenience of the patient so that he can place two fingers from each hand, one each on the finger touchpads 2-5. Preferably, the outermost finger touchpads 2 and 5 are used to generate the necessary signals. In this case, the center two finger touchpads 3 and 4 can be electrically connected together as shown in FIG. 2 since they provide the reference for the outer two finger touchpads 2 and 5.

The communications station 8 is preferably located, in part, on the upper portion of face 6 of the unit 1, at the end most distant from the finger touchpads 2-5. The communications station comprises a microphone (not shown) for receiving audio signals from the telephone handset and a speaker 10 for transmitting audio signals to the microphone in the receiver of the telephone handset. One the back edge of the unit 1 is mounted the microphone for detecting the multi-frequency tones sent from the receiving center. The communications station also comprises a visual display 12 located above the touchpads 2-5. Preferably, the visual display 12 comprises a plurality of lights 13, 14, 15, and 16 used in connection with printed words. When a light is activated, corrective action, as indicated by the associated printed words, needs to be taken.

The unit 1 can also have jacks 18 for connecting the unit to the standard finger, wrist and/or chest electrodes. As shown in FIG. 1 these jacks are located on the side of unit 1, but could be located at other positions on the unit. Similarly, the layout of the face 6 of the unit 1 could be arranged differently without impairing the function of the monitoring device.

Within the unit 1 is the electronic circuitry which detects and transmits the pacemaker signals as well as the patient's pulse, as well as the circuitry which receives the feedback signals from the receiving center and activates the visual display 12. FIG. 2 shows the detection circuit 20 and the transmission circuit 21 which form the detection and transmission circuit 19. Preferably, the detection circuit 20 comprises a differential amplifier 22 electrically connected to a shaper 23. The shaper preferably comprises an integrator circuit and a filter (not shown) to properly shape the input signal for the transmission circuit 21. Preferably the differential amplifier 22 comprises two op amps 24 and 25, each one connected in a voltage follower configuration to one of the finger touchpads, 2 and 5, respectively, to provide a high impedance input into an op amp 26 operated in the differential configuration. The output of the differential op amp 26 is fed to another op amp 27 to increase the signal fed to the transmission circuit 21.

The transmission circuit 21 preferably comprises a voltage controlled oscillator 28 ("VCO") and an op amp amplifier used to drive the speaker 10 of the communications station 8. The voltage controlled oscillator 28 is connected to two potentiometers 30 and 31 to adjust the oscillator 28 and control the signal which is fed into op amp 29 to activate the speaker 10.

Figure 3:
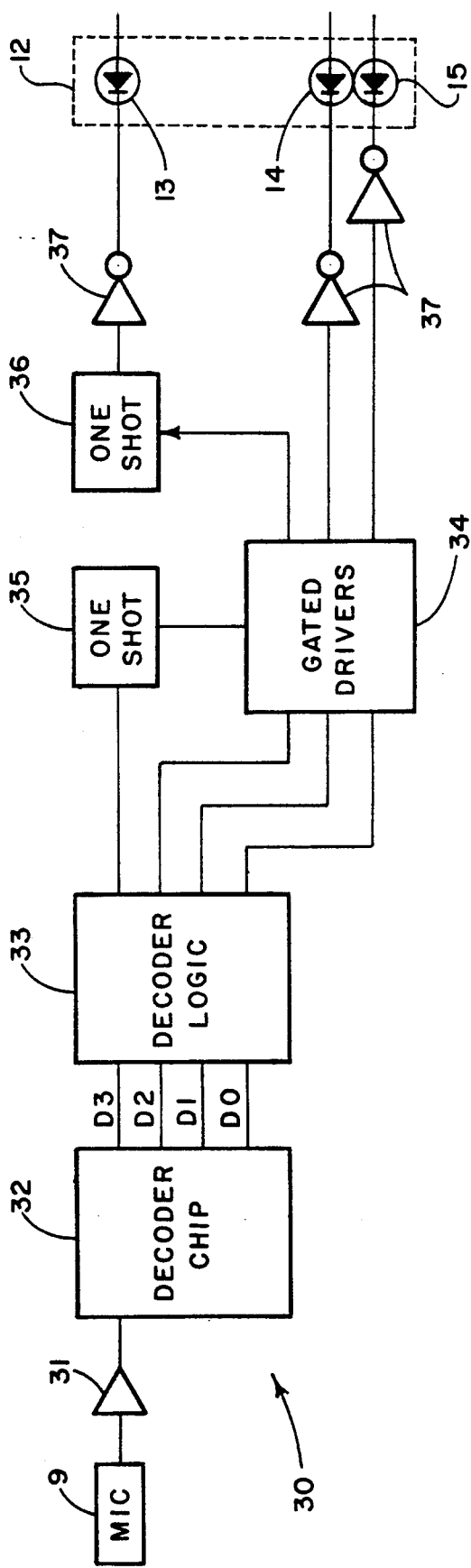
FIG. 3 is a block diagram of the decoder circuit.

The decoder circuit 30 which is shown in FIG. 3 is connected between the microphone (not shown) on the back edge of the unit and the visual display 12. A multi-frequency signal from the receiving center, such as one generated by the nurse or operator pressing one of the buttons on a telephone, is received by the microphone and amplified by the decoder circuit 30 using op amp 31 and then fed into a decoder chip 32 such as the 8870 made by Mitel. The output of the decoder chip 32 is preferably in hexadecimal format and is fed to the decoder logic 33 consisting of gates and gates. The output of the decoder logic 33 is fed to the gated drivers 34 which control whether the lights in of the visual display are on or off. Preferably the lights 13-15 are different color LED's for ease of differentiation by the patient and their low power consumption. Two one-shots 35 and 36 help to generate one of the feedback signals. Also, inverters 37 are part of the decoder circuit 30 and enable the gated drivers 34 to turn on the LED's with a positive output.

Figure 4:
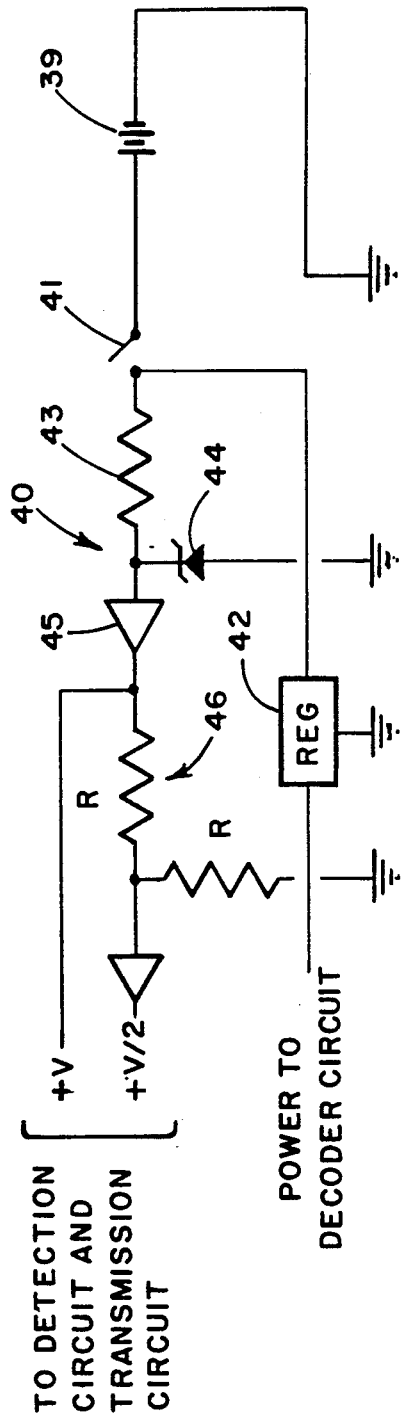
FIG. 4 is a block diagram of the power supply circuit.

The unit 1 derives its power from a 9 volt battery 39 through the power supply circuit 40 shown in FIG. 4. First, the battery 39 is connected through an on/off switch 41. When the switch 41 is closed, the 9 volts from the battery is applied to a 5 volt regulator 42 such as the 78L05 with the output of this regulator 42 used to provide the power to the decoder circuit 30. It is desirable to keep the power to the decoder circuit 30 separate from the power to the detection and transmission circuit 19. As a result, separately connected to the switch 41 is the power circuit for the detection and transmission circuit 19 which comprises a limiting resistor 43 and a zener diode 44 which preferably caps the voltage from the battery 39 at 5.1 volts. This voltage is then fed through an op amp 45 in a voltage follower configuration and then to a resistive voltage divider 46 having equal resistors R to generate output voltages of V and V/2 where V is preferably 5 volts. The V/2 voltage from the voltage divider 46 is first fed through an op amp 47 in the voltage follower configuration before being connected to finger touchpads 3 and 4.

Figure 5:
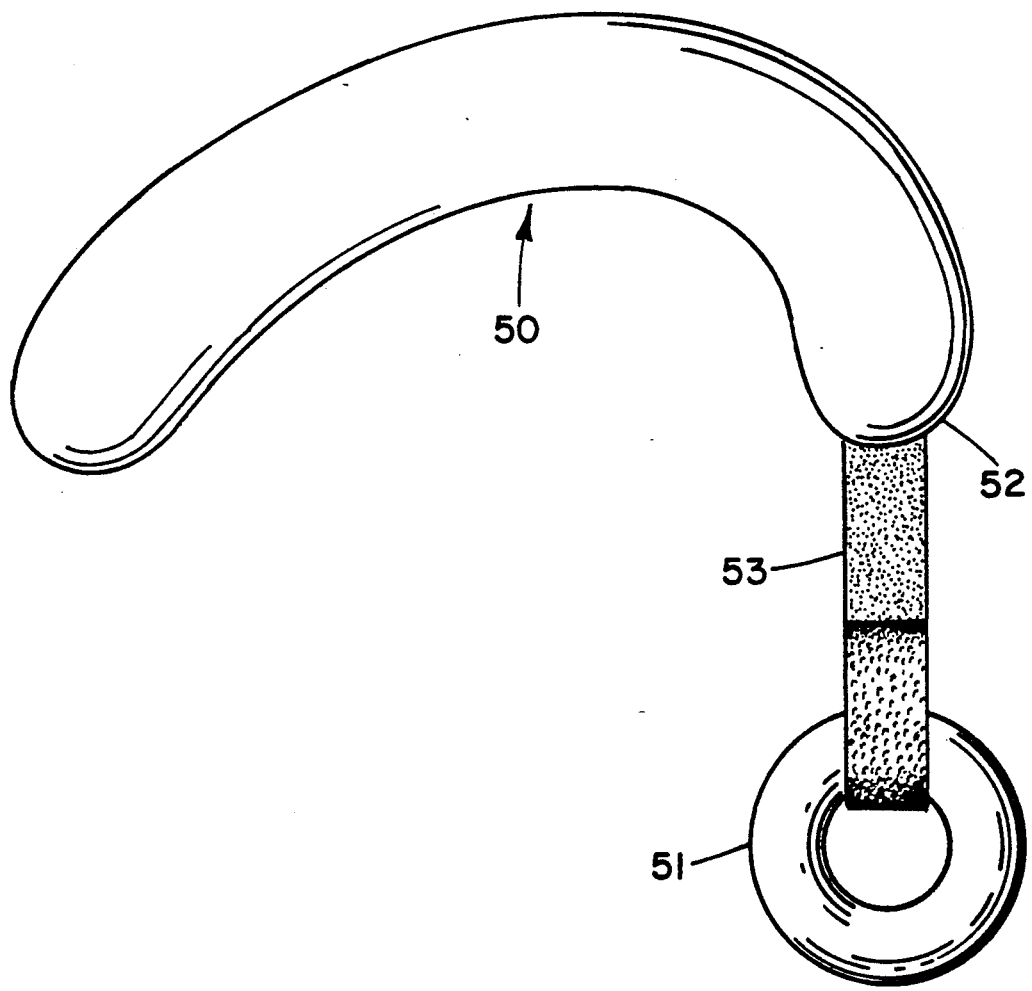
FIG. 5 is a perspective view of the shoulder harness for supporting the magnet.

FIG. 5 shows a perspective view of one embodiment of a magnet support device, namely the shoulder harness 50 for supporting the magnet 51 used to cause the pacemaker to operate in the magnetic mode. Preferably, the shoulder harness 50 is made from a flexible plastic material which is preformed into the shape of a curve which can easily fit over the shoulder of the patient and remain in place. The front portion 52 of the shoulder harness 50 is preferably tapered and contains an adhesive type material on the underside thereof (not shown). Preferably the adhesive type material is a set of hook and loop fasteners such as that sold under the trademark Velcro ®. Typically, the magnet 51 used for monitoring the magnetic rate of a pacemaker is a donut shape magnet. This magnet 51 can be directly attached to the adhesive material on the underside of the shoulder harness. To make the harness 50 more versatile, and the magnet adjustable, the magnet preferably has a loop 53 of Velcro ® around it which can matingly engage the Velcro ® strip placed on the underside of the tapered end 52 of the shoulder harness 50. Other types of magnet supporting devices can also be used such as a piece of clothing worn by the patient, such as a halter top, which has a pocket therein for receiving and holding the magnet.

In a preferred embodiment of the visual display 12, green, yellow and red LEDs are used as lights 13-15. The visual display 12 is controlled by the operator at the receiving center. The green LED 14 will remain lit next to the words "proper transmission" when the monitor is being used properly. The yellow LED 15 will light next to the words "press harder with fingertips" when additional pressure is required. This is an important capability since the strength of the patient's pulse will vary with each patient. The red LED 13 will light next to the words "pick up phone" when the receiving center is not obtaining a proper transmission or desires to communicate directly with the patient.

As indicated earlier, the LED's 13-15 can be controlled through the telephone line by the operator at the receiving center. For example, if the tracing is not being properly received, the operator can deactivate the green LED 14 signifying a "proper transmission" and activate the red 13 LED signifying an error and requesting the patient to "pick up phone". This can be done by simply pressing a key on the telephone at the receiving center followed by the star button. Similarly, the yellow LED signifying "press harder with fingertips" can be controlled in the same manner, again by pressing keys on the telephone at the receiving center thereby saving valuable time and instructing the patient without having to pick up the telephone. Of course, the present invention can also incorporate the loud buzzer as a back-up for vision impaired patients.

Additionally, a fourth LED 16 is provided which is not controlled by the operator at the receiving center. This LED is used to advise the patient as to whether the battery in the unit is low. A blue LED can be used for this purpose. Preferably the blue LED is on when the battery has sufficient voltage but blinks when it does not. The circuit used to generate the signal to the blue LED 16 is very straightforward and consists of a 555 timer operating in the a-stable configuration and connected to the blue LED 16 in parallel with a comparator. The comparator compares the voltage from a resistor divider connected to the battery 39 with the voltage provided by the power supply circuit 40 to the detection and transmission circuit 19. As long as these two voltages are the same, the comparator prevents the blue LED 16 from blinking. If the voltage is different, however, the comparator enables the 555 timer to control the blue LED 16 and causes it to blink on and off.

While a presently preferred embodiment of practicing the invention has been shown and described with particularity in connection with the accompanying drawings, the invention may be otherwise embodied within the scope of the following claims.

What is claimed is:

1. A remote pacemaker monitoring device for a patient comprising a portable unit wherein at least three electrically conductive touchpads, a transmitter, an audio detector for detecting signals transmitted from a receiving center and a visual display are located on an outside surface of the unit; wherein a detection and transmission circuit is electrically connected between the touchpads and the transmitter which is capable of detecting pacemaker signals and transmitting them to a receiving center via a communication means; and wherein a decoder circuit is electrically connected between the visual display and the audio detector which is capable of providing visual feedback to the patient via the communication means for the receiving center.

2. The device as described in claim 1 wherein the communication means is a telephone system.

3. The device as described in claim 2 wherein the touchpads are located on the face of the unit in a U-shaped or V-shaped configuration.

4. The device as described in claim 3 further comprising a fourth touchpad and wherein two of the touchpads are electrically connected together to form a common reference.

5. The device as described in claim 4 wherein the visual display is located on the face of the unit.

6. The device as described in claim 5 wherein the transmitter comprises an output speaker.

7. The device as described in claim 6 further comprising a sound generating device for providing audio feedback to the patient which corresponds to the visual feedback.

8. The device as described in claim 6 further comprising a magnet and a magnet supporting device which adjustably located the magnet over the patient's pacemaker causing it to operate in the magnetic mode.

9. The device as described in claim 8 wherein the magnet supporting device is a shoulder harness to which the magnet can be detachably connected by means of hook and loop fasteners.

10. The device as described in claim 6 further comprising a plurality of jacks for connecting external electrodes to the unit.

11. A remote cardiac monitoring device for a patient comprising a portable unit wherein at least three electrically conductive touchpads, a transmitter, an audio detector for detecting signals transmitted form a receiving center and a visual display are located on an outside surface of the unit; wherein a detection and transmission circuit is electrically connected between the touchpads and the transmitter which is capable of detecting a patient's pulse and transmitting it to a receiving center via a communication means; and wherein a decoder circuit is electrically connected between the visual display and the audio detector which is capable of providing visual feedback to the patient via the communication means from the receiving center.

12. The device as described in claim 11 wherein the communication means is a telephone system.

13. The device as described in claim 12 wherein the touchpads are located on the face of the unit in a U-shaped or V-shaped configuration.

14. The device as described in claim 13 further comprising a fourth touchpad and wherein two of the touchpads are electrically connected together to form a common reference.

15. The device as described in claim 14 wherein the visual display is located on the face of the unit.

16. The device as described in claim 15 wherein the transmitter comprises and output speaker.

17. The device as described in claim 16 further comprising a sound generating device for providing audio feedback to the patient which corresponds to the visual feedback.

18. The device as described in claim 16 further comprising a plurality of jacks for connecting external electrodes to the unit.

* * * * *